United States Patent [19]

Negi et al.

[11] Patent Number: 4,513,145
[45] Date of Patent: Apr. 23, 1985

[54] 2-METHYLCHROMONE DERIVATIVES AND PROCESS FOR THEIR PREPARATION

[75] Inventors: Shigeto Negi; Seiichiro Nomoto; Takashi Kamiya; Yoshimasa Machida; Isao Saito; Kyosuke Kitoh, all of Ibaraki, Japan

[73] Assignee: Eisai Co., Ltd., Tokyo, Japan

[21] Appl. No.: 457,394

[22] Filed: Jan. 12, 1983

[30] Foreign Application Priority Data

Dec. 28, 1982 [JP] Japan ................... 57-232443

[51] Int. Cl.³ ................... C07D 311/22
[52] U.S. Cl. ................... 549/402; 544/27; 544/28
[58] Field of Search ................... 549/402

[56] References Cited

U.S. PATENT DOCUMENTS 4,309,354 1/1982 Nomoto et al. ................... 549/402
4,331,606 5/1982 Nomoto et al. ................... 549/402

FOREIGN PATENT DOCUMENTS 57-59883 4/1982 Japan ................... 549/402

Primary Examiner—Nicky Chan
Attorney, Agent, or Firm—Wenderoth, Lind & Ponack

[57] ABSTRACT

A novel 2-methylchromone derivative represented by the general formula:

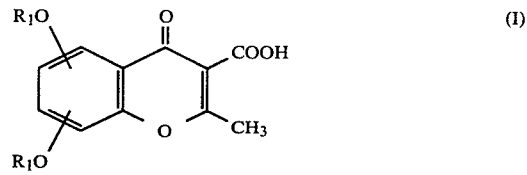

wherein $R_1$ means a hydrogen atom or a lower alkanoyl group. The above derivative is a useful intermediate for the synthesis of cephem activities, which are also effective against infections of the urinary tract, etc. A preparation process of the above chromone derivative is also disclosed.

4 Claims, No Drawings

2-METHYLCHROMONE DERIVATIVES AND PROCESS FOR THEIR PREPARATION

BACKGROUND OF THE INVENTION (a) Field of the Invention

This invention relates to pharmaceutical intermediates and their preparation process, and more specifically to novel 2-methylchromone derivatives represented by the general formula:

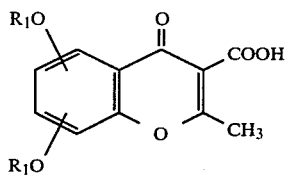

wherein $R_1$ means a hydrogen atom or a lower alkanoyl group and their preparation process.

As exemplary lower alkanoyl groups represented by $R_1$, may be mentioned acetyl, propionyl, butyryl and isobutyryl groups and the like.

(b) Description of the Prior Art

As have been disclosed in Japanese Patent Laid-open Nos. 136292/80, 5487/81, 73087/81, 122384/81 and 45185/82, 7-phenylacetamido-3-cephem derivatives having the chromone nucleus have been known in recent years. These compounds have strong antibacterial activities against gram-negative bacteria, notably, *Pseud. aeruginosa, Kleb. pneumoniae, Ser. marcescens* and the like and are effective against a variety of infectious diseases. However, each of these compounds is primarily excreted into bile and only a little portion thereof is excreted into urine when administered. These compounds are still effective against infections of the urinary tract owing to their very strong antibacterial activities although only minor portions thereof are excreted into urine as mentioned above. However, there is a standing demand for the development of 7-phenylacetamido-3-cephem derivatives having higher excretion rates into urine.

SUMMARY OF THE INVENTION

Each of the above-described known compounds has a chromone nucleus unsubstituted at its 2-position. The present inventors have unexpectedly found that the excretion rate into urine can be improved when the chromone nucleus without 2-substituent is replaced by another chromone nucleus substituted with a methyl group at its 2-position, thereby leading to the completion of this invention. Accordingly, the compounds of this invention are useful as pharmaceutical intermediates.

In one aspect of this invention, there is thus provided a 2-methylchromone derivative represented by the general formula:

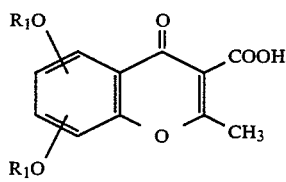

wherein $R_1$ means a hydrogen atom or a lower alkanoyl group.

In another aspect of this invention, there is also provided a process for preparing a compound represented by the following formula:

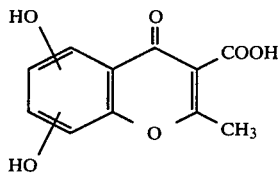

which comprises reacting an acid with a compound represented by the general formula:

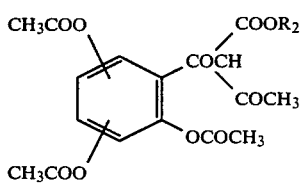

wherein $R_2$ means a lower alkyl group.

In a further aspect of this invention, there is also provided a process for preparing a compound represented by the general formula:

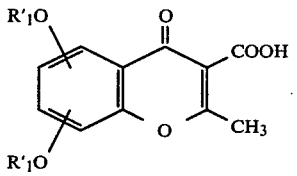

wherein $R_1'$ means a lower alkanoyl group, which comprises reacting a compound represented by the general formula:

wherein $R_1'$ has the same meaning as defined above or its reactive derivative with a compound represented by the following formula:

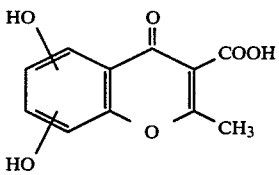

The above and other objects, features and advantages of the present invention will become apparent from the following description and the appended claims.

DETAILED DESCRIPTION OF THE INVENTION AND PREFERRED EMBODIMENTS

The compounds according to this invention may be prepared, for example, in accordance with the following reaction scheme:

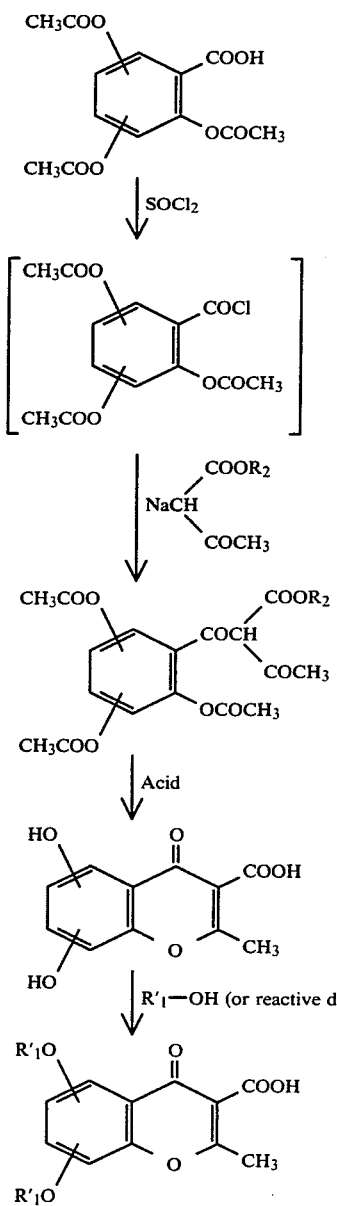

wherein $R_1'$ means a lower alkanoyl group and $R_2$ denotes a lower alkyl group.

Illustrative lower alkanoyl groups represented by $R_1'$ include acetyl, propionyl, butyryl and isobutyryl groups and the like. On the other hand, as exemplary lower alkyl groups represented by $R_2$, may be mentioned methyl, ethyl, propyl, isopropyl, butyl, isobutyl, sec-butyl and tert-butyl groups and their analogous groups.

The acid chloride represented by the formula (III) may be obtained in a manner commonly known in the art, namely, by heating the carboxylic acid of the formula (II) and thionyl chloride in an inert solvent. The compound represented by the formula (III) can be used in the subsequent reaction without isolating the same from the reaction mixture.

The compound of the general formula (IV) may be obtained by reacting a lower alkyl ester of acetoacetic acid with sodium hydride in an inert solvent. The compound of the general formula (V) can be prepared by reacting the compound of the general formula (IV) and the compound of the formula (III) at room temperature.

The compound of the formula (I)-1, which pertains the present invention, can be obtained by reacting an acid with the compound of the general formula (V). As such an acid, may be mentioned hydrochloric acid, sulfuric acid, nitric acid or the like. The above reaction is carried out in an inert solvent which may, for example, be tetrahydrofuran, dioxane, dimethoxyethane, dimethylformamide or a mixed solvent thereof. The reaction temperature may suitably range from 50° C. to 100° C.

The compound of the general formula (I)-2, which also relates to the present invention, may be obtained by reacting $R_1'$-OH, which is a carboxylic acid, or its reactive derivative with the compound represented by the formula (I)-1. This reaction may be conducted in a manner generally employed in esterification reactions. It is preferable to use a reactive derivative of $R_1'$-OH. As illustrative reactive derivatives, may be mentioned acid halides such as acid chlorides and acid bromides; symmetric acid anhydrides; mixed-acid anhydrides with chlorocarbonic acid esters; etc. As exemplary solvents useful in the practice of the above esterification reaction, may be mentioned dimethylformamide, benzene, ethyl ether, methylene chloride, chloroform, ethyl acetate and mixed solvents thereof. The reaction temperature may suitably range from 0° C. to 50° C.

The compounds of the present invention may be used as intermediates, for example, as follows:

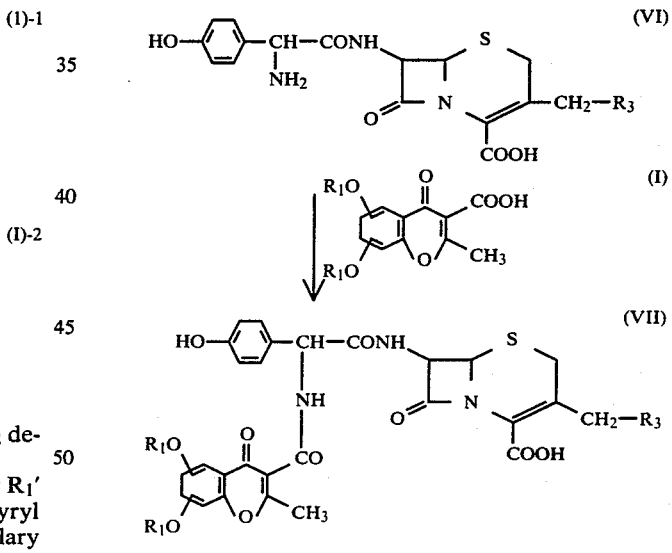

wherein $R_1$ has the same meaning as defined above and $R_3$ means a nitrogen-containing heterocyclic-thio group which may optionally contain one or more substituent groups or acetoxy group.

By reacting the compound of the general formula (VI) or its salt with the compound of the general formula (I) or its reactive derivative, it is possible to obtain the compound of the general formula (VII) or its non-toxic salt which is useful as an antibacterial agent.

The above-described reaction between the compound of the general formula (I) and the compound represented by the general formula (VI) may be carried out in a manner routinely employed in amidation reactions. When the compound of the general formula (I) of this invention is employed as it is, it is preferred to carry out the reaction in the presence of a condensing agent such as N,N'-dicyclohexylcarbodiimide, N-cyclohexyl-N'-(2-morpholinoethyl)carbodiimide, ethyl polyphosphate, phosphorus oxychloride, oxalyl chloride or the like.

Alternatively, the compound of the general formula (I) of the present invention may first of all be converted to its reactive derivative and the resulting reactive derivative may then be reacted with the compound of the general formula (VI) or its salt. As exemplary reactive derivatives, may be mentioned acid halides such as acid chlorides and acid bromides; symmetric acid anhydride; mixed-acid anhydrides with chlorocarbonic acid ester, trimethylacetic acid or diphenylacetic acid; active esters with 2-mercaptopyridine, cyanomethanol, p-nitrophenol, 2,4-dinitrophenol, pentachlorophenol or the like; active acid amides such as N-acylsaccharin or N-acylphthalide.

Having generally described the invention, a more complete understanding can be obtained by reference to the following examples and preparations, which are provided herein for purposes of illustration only and are not intended to be limiting the scope of the invention.

EXAMPLE 1

6,7-Dihydroxy-2-methylchromone-3-carboxylic acid

A mixture of 2,4,5-triacetoxybenzoic acid [2.4 g (8.1 millimoles)], thionylchloride (2 ml), dimethylformamide (several drops) and dry benzene (50 ml) was refluxed for 1 hour. The solvent was evaporated under reduced pressure, and anhydrous ethyl ether (120 ml) was added to the residue to give Solution A.

Sodium hydride [776 mg (16.2 millimoles)] was added to anhydrous ethyl ether (150 ml) with stirring, followed by addition of ethyl acetoacetate [2.08 ml (16 millimoles)] to obtain Solution B.

Solution A was added dropwise to Solution B with vigorous stirring. Following the dropwise addition of Solution A, the resulting mixture was stirred for 5 hours, followed by addition of water (100 ml). The ethyl ether layer was washed successively with 1N-HCl, water and a saturated aqueous solution of sodium chloride and then dried over magnesium sulfate. The thus-dried ethyl ether solution was concentrated under reduced pressure and the residue was purified by silica gel column chromatography (benzene:ethyl acetate=4:1), to obtain ethyl 1-(2,4,5-triacetoxybenzoyl)-3-oxobutanoate as white crystals (2.4 g).

A mixture of the above-obtained compound [1.6 g (4 millimoles)], tetrahydrofuran (80 ml) and 3N-HCl (250 ml) was refluxed for 3 days and then cooled to room temperature. Ethyl acetate (250 ml) was added to the mixture and the organic layer was then washed successively with water and a saturated aqueous solution of sodium chloride. After drying the organic layer over magnesium sulfate, it was concentrated under reduced pressure. Ethyl ether was then added to the residue to cause white crystals to precipitate. The white crystals were collected by filtration to afford the desired product (790 mg).

Infrared absorption spectrum [cm$^{-1}$, Nujol (trade mark)]: 1705, 1610, 1590.

NMR spectrum ($\delta$, DMSO-d$_6$): 2.77 (3H, s), 7.02 (1H, s), 7.45 (1H, s).

EXAMPLE 2

6,7-diacetoxy-2-methylchromone-3-carboxylic acid

A mixture of 6,7-dihydroxy-2-methylchromone-3-carboxylic acid (2.24 g), dimethylformamide (30 ml), ethyl acetate (10 ml), pyridine (2.3 ml) and acetic anhydride (2.3 ml) was stirred at room temperature for 3 hours. Ethyl acetate (100 ml) was added to the reaction mixture, and the organic layer was washed successively with 6N-HCl and water, and thereafter dried over anhydrous magnesium sulfate. The solvent was evaporated and ethyl ether was added to the residue. The resulting solid was collected by filtration. It was washed with a 1:1 mixed solvent of ethyl acetate and ethyl ether and then dried, to obtain the desired product (1.93 g).

Infrared absorption spectrum [cm$^{-1}$, Nujol (trade mark)]: 1780, 1750, 1720, 1605.

NMR spectrum ($\delta$, DMSO-d$_6$): 2.31 (3H, s), 2.34 (3H, s), 2.60 (3H, s), 7.74 (1H, s), 7.91 (1H, s).

EXAMPLE 3

7,8-Dihydroxy-2-methylchromone-3-carboxylic acid

A mixture of 2,3,4-triacetoxybenzoic acid (7.4 g), thionyl chloride (2.18 ml), dimethylformamide (0.04 ml) and benzene (150 ml) was refluxed for 1 hour. After cooling the reaction mixture, the solvent was evaporated and tetrahydrofuran (10 ml) was added to the residue to obtain Solution A.

Sodium hydride (2.40 g) was added to anhydrous tetrahydrofuran (25 ml). Ethyl acetoacetate (6.37 ml) was then added dropwise to the above mixture, to obtain Solution B.

Solution A was added to Solution B and the resulting mixture was stirred for 30 minutes. The solvent was evaporated and the residue was taken up in ethyl acetate (100 ml). After cooling the resulting ethyl acetate solution with ice, 1N-HCl (20 ml) was added to the solution with stirring. The ethyl acetate layer was washed successively with water and a saturated aqueous solution of sodium chloride, and then dried over anhydrous magnesium sulfate. The solvent was evaporated and ethyl ether was added to the residue. The resulting solid was collected by filtration, washed with ethyl ether and dried, to obtain ethyl 2-(2,3,4-triacetoxybenzoyl)-3-oxobutanoate (6.09 g). Furthermore, the same compound was also obtained in an amount of 0.41 g as second crop from the mother liquor, thereby making the total yield of ethyl 2-(2,3,4-triacetoxybenzoyl)-3-oxobutanoate be 6.50 g.

The thus-obtained 2-(2,3,4-triacetoxybenzoyl)-3-oxobutanoate (3.2 g) was taken up in a mixture of tetrahydrofuran (160 ml) and 3N-HCl (160 ml) and agitated at 70° C. for 20.5 hours. The reaction mixture was concentrated to 20 ml and the resulting precipitate was collected by filtration. It was washed with water and then dried to give the desired product (0.94 g).

Infrared absorption spectrum [cm$^{-1}$, Nujol (trade mark)]: 1785, 1720, 1660.

NMR spectrum ($\delta$, DMSO-d$_6$): 2.73 (3H, s), 6.98 (1H, d, J=8 Hz), 7.43 (1H, d, J=8 Hz).

EXAMPLE 4

7,8-Diacetoxy-2-methylchromone-3-carboxylic acid

A mixture of 7,8-dihydroxy-2-methylchromone-3-carboxylic acid (0.9 g), dimethylformamide (10 ml), pyridine (0.92 ml) and acetic anhydride (1.2 ml) was stirred at room temperature for 4 hours. Ethyl acetate (100 ml) was added to the liquid reaction mixture, and the organic layer was washed successively with 6N-HCl and water, and then dried over anhydrous magnesium sulfate. The solvent was evaporated and ethyl ether was added to the residue. The resulting solid was collected by filtration and then washed with a 1:1 mixed solvent of ethyl acetate and ethyl ether, followed by drying to afford the desired product (0.534 g).

Infrared absorption spectrum [cm$^{-1}$, Nujol (trademark)]: 1775, 1730, 1605.

NMR spectrum ($\delta$, DMSO-d$_6$):
2.24 (3H, s), 2.42 (3H, s), 2.54 (3H, s), 7.45 (1H, d, J=8 Hz), 7.97 (1H, d, J=8 Hz).

Preparation 1

7$\beta$-[D-2-(6,7-Dihydroxy-2-methylchromone-3-carboxamido)-2-(4-hydroxyphenyl)acetamido]-3-(1-carboxymethyl-5-tetrazolyl)thiomethyl-3-cephem-4-carboxylic acid and its disodium salt (a) 7$\beta$-[D-2-(6,7-Dihydroxy-2-methylchromone-3-carboxamido)-2-(4-hydroxyphenyl)acetamido]-3-(1-carboxymethyl-5-tetrazolyl)thiomethyl-3-cephem-4-carboxylic acid:

A mixture of 6,7-dihydroxy-2-methylchromone-3-carboxylic acid [347 mg (1.47 millimoles)], which had been obtained in Example 1, and thionyl chloride (16 ml) was refluxed for 1 hour. The remaining thionyl chloride was evaporated and then dried in vacuo, to obtain 6,7-dihydroxy-2-methylchromone-3-carbonyl chloride. The compound was dissolved in dry ethyl acetate (35 ml) to form the acid chloride solution.

A mixture of trifluoroacetic acid salt of 7$\beta$-[D-2-amino-2-(4-hydroxyphenyl)acetamido]-3-(1-carboxymethyl-5-tetrazolyl)thiomethyl-3-cephem-4-carboxylic acid [280 mg (0.441 millimoles)], N,O-bis(trimethylsilyl)acetamide (0.5 ml) and ethyl acetate (10 ml) was stirred at room temperature for 20 minutes. The above-formed acid chloride solution (10 ml) was then added to the above mixture and the resulting mixture was stirred for 1 hour. The reaction mixture was then washed successively with 1N-HCl, water and a saturated aqueous solution of sodium chloride, dried over magnesium sulfate and thereafter concentrated under reduced pressure. To the residue was added successively ethyl acetate (2 ml) and ethyl ether (50 ml). The resulting precipitate was collected by filtration, to obtain the desired product (227 mg).

Infrared absorption spectrum [cm$^{-1}$, Nujol (trade mark)]: 1760, 1710, 1660.

NMR spectrum ($\delta$, DMSO-d$_6$): 2.42 (3H, s), 3.48 (1H, d, J=18 Hz), 3.71 (1H, d, J=18 Hz), 4.18 (1H, d, J=13 Hz), 4.47 (1H, d, J=13 Hz), 4.98 (1H, d, J=5 Hz), 5.30 (2H, s), 5.60 (1H, d, J=8 Hz), 5.71 (1H, dd, J=5 Hz, 8 Hz), 6.70 (1H, d, J=8 Hz), 6.88 (1H, s), 7.26 (2H, d, J=8 Hz), 7.32 (1H, s), 9.27 (1H, d, J=8 Hz), 9.98 (1H, d, J=8 Hz).

Antibacterial activities (MIC, $\mu$g/ml):
Escher. coli N1HJ—0.1
Pseud. aeruginosa EP-172—0.4
Kleb. pneumoniae EK-6—$\leq$0.05
Pseud. maltophillia EP-12—25
Ser. marcescens ES-75—$\leq$0.05
Proteus morganii EP-14—0.8

(b) Disodium 7$\beta$-[D-2-(6,7-dihydroxy-2-methylchromone-3-carboxamido)-2-(4-hydroxyphenyl)acetamido]-3-(1-carboxymethyl-5-tetrazolyl)thiomethyl-3-cephem-4-carboxylate:

The compound obtained in the above (a) [150 mg (0.203 millimoles)] was dissolved in methanol (10 ml), to which was added a methanol solution (2 ml) containing sodium acetate (35 mg). After 20 minutes, the solvent was evaporated under reduced pressure and ethanol (20 ml) was added to the residue. The resulting precipitate was collected by filtration, washed with ethyl ether, and then dried to afford the desired product (163 mg).

Infrared absorption spectrum [cm$^{-1}$, Nujol (trade mark)]: 1755, 1620.

NMR spectrum ($\delta$, DMSO-d$_6$): 3.61 (3H, s), 4.58 (2H, s), 4.86 (1H, d, J=5 Hz), 5.40-5.70 (2H, m), 6.69 (2H, d, J=8 Hz), 6.71 (1H, s), 7.20 (1H, s), 7.25 (2H, d, J=8 Hz).

Antibacterial activities (MIC, $\mu$g/ml):
Escher. coli N1HJ—0.1
Pseud. aeruginosa EP-172—0.4
Kleb. pneumoniae EK-6—$\leq$0.05
Pseud. maltophillia EP-12—25
Ser. marcescens ES-75—$\leq$0.05
Proteus morganii EP-14—0.8

Excretion rate into urine:

ICR male mice (body weight: 20–30 g) were used. The above-obtained disodium salt was dissolved in an M/15 phosphate buffer (pH 7.0) and administered in an amount of 20 mg/Kg by the subcutaneous route. Urine was collected up to 6 hours after the administration. The concentration of the disodium salt was determined by the bioassey technique (the agar-well method) using Pseudomonas aeruginosa as a test microorganism. On the basis of the thus-determined concentration data, its excreted quantity was obtained. The percentage of the excreted quantity was then calculated based on the amount administered, thereby determining its excretion rate.

| | Excretion rate into urine |
|---|---|
| Disodium 7$\beta$-[D-2-(6,7-dihydroxy-2-2-methylchromone-3-carboxamido)-2-(4-hydroxyphenyl)acetamido]-3-(1-carboxymethyl-5-tetrazolyl)thiomethyl-3-cephem-4-carboxylate | 1.51% |
| Disodium 7$\beta$-[D-2-(6,7-dihydroxy-chromone-3-carboxamido)-2-(4-hydroxyphenyl)acetamido]-3-(1-carboxymethyl-5-tetrazolyl)thiomethyl-3-cephem-4-carboxylate (Control Compound) | 0.3% |

Having now fully described the invention, it will be apparent to one of ordinary skill in the art that many changes and modifications can be made thereto without departing from the spirit or scope of the invention as set forth herein.

What is claimed is:

1. A 2-methylchromone derivative represented by the general formula:

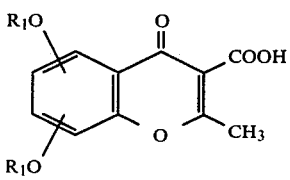

wherein $R_1$ means a hydrogen atom or a lower alkanoyl group.

2. A 2-methylchromone derivative as claimed in claim 1, wherein $R_1$ in the formula means a hydrogen atom or acetyl group.

3. A 2-methylchromone derivative as claimed in claim 1, which is 6,7-dihydroxy-2-methylchromone-3-carboxylic acid.

4. A 2-methylchromone derivative as claimed in claim 1, which is 6,7-diacetoxy-2-methylchromone-3-carboxylic acid.

* * * * *